United States Patent
Zhang et al.

(10) Patent No.: US 12,181,473 B2
(45) Date of Patent: Dec. 31, 2024

(54) TIME-RESOLVED FLUORESCENCE IMMUNOCHROMATOGRAPHIC KIT FOR SIMULTANEOUS DETECTION OF MIXED CONTAMINATION OF FIVE MYCOTOXINS SUCH AS AFLATOXIN B1 AND APPLICATION THEREOF

(71) Applicant: OIL CROPS RESEARCH INSTITUTE, CHINESE ACADEMY OF AGRICULTURAL SCIENCES, Hubei (CN)

(72) Inventors: Zhaowei Zhang, Hubei (CN); Peiwu Li, Hubei (CN); Qi Zhang, Hubei (CN); Du Wang, Hubei (CN); Wen Zhang, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 1323 days.

(21) Appl. No.: 16/492,303

(22) PCT Filed: Mar. 7, 2018

(86) PCT No.: PCT/CN2018/078198
§ 371 (c)(1),
(2) Date: Jan. 24, 2020

(87) PCT Pub. No.: WO2018/161905
PCT Pub. Date: Sep. 13, 2018

(65) Prior Publication Data
US 2021/0132066 A1    May 6, 2021

(30) Foreign Application Priority Data
Mar. 7, 2017 (CN) .......................... 201710131289.4

(51) Int. Cl.
*G01N 33/543* (2006.01)
*G01N 21/64* (2006.01)
*G01N 33/569* (2006.01)

(52) U.S. Cl.
CPC ... *G01N 33/54388* (2021.08); *G01N 21/6408* (2013.01); *G01N 33/56961* (2013.01); *G01N 2333/38* (2013.01); *G01N 2458/40* (2013.01)

(58) Field of Classification Search
CPC ......... G01N 33/54388; G01N 21/6408; G01N 33/56961; G01N 2333/38; G01N 2458/40;
(Continued)

(56) References Cited

FOREIGN PATENT DOCUMENTS

| CN | 102747043 A | 10/2012 |
|---|---|---|
| CN | 103215231 A | 7/2013 |
| CN | 103217531 A | 7/2013 |
| CN | 103232975 A | 8/2013 |

(Continued)

OTHER PUBLICATIONS

Goel et al. ("Plasticity within the Antigen Combining Site May Manifest as Molecular Mimicry in the Humoral Immune Response," The Journal of Immunology (2004), 173(12):7358-7367) (Year: 2004).*

(Continued)

*Primary Examiner* — Christopher L Chin
(74) *Attorney, Agent, or Firm* — Tim Tingkang Xia, Esq.; Locke Lord LLP

(57) ABSTRACT

A time-resolved fluorescence immunochromatographic kit for simultaneous detection of mixed contamination of five mycotoxins such as aflatoxin B1 and an application thereof are disclosed. The kit comprises a time-resolved fluorescent immunochromatographic test strip and sample reaction vials each containing a europium-labeled monoclonal antibody lyophilized product; wherein the fluorescent test strip comprises a PVC substrate, and a surface of the PVC substrate (Continued)

is adhered with a water absorbing pad (1), a detection pad (2) and a sample pad (3) from top to bottom, adjacent pads being connected and overlapping at connections. The detection pad (2) adopts a nitrocellulose membrane as the base thereof and is arranged with a lateral quality control line (5) and five detection lines (5, 6, 7, 8, 9) from top to bottom each covered by a bovine serum albumin conjugate of each toxin. The fumonisin B1 monoclonal antibody is generated by the hybridoma cell strain Fm7A11 having China Center for Type Culture Collection (CCTCC) accession number C201636. The kit is applicable to simultaneous detection of mixed contamination of aflatoxin B1, fumonisin B1, ochratoxin A, zearalenone and sterigmatocystin.

4 Claims, 1 Drawing Sheet

Specification includes a Sequence Listing.

(58) Field of Classification Search
CPC ....... G01N 21/8483; G01N 2021/7759; G01N 33/558; G01N 2021/7786; G01N 33/577; G01N 33/54387; G01N 33/54389; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

FOREIGN PATENT DOCUMENTS

| CN | 103278631 A | 9/2013 |
| CN | 103808925 A | 5/2014 |
| CN | 103849604 A | 6/2014 |
| CN | 105372416 A | 3/2016 |
| CN | 106932370 A | 7/2017 |

OTHER PUBLICATIONS

Lloyd et al. ("Modelling the human immune response: performance of a 1011 human antibody repertoire against a broad panel of therapeutically relevant antigens," Protein Engineering, Design & Selection (2009), 22(3):159-168) (Year: 2009).*

Edwards et al. ("The remarkable flexibility of the human antibody repertoire; isolation of over one thousand different antibodies to a single protein, BlyS," Journal of Molecular Biology (2003), 334:103-118) (Year: 2003).*

Yao, Jingjing et al., "Colloidal Gold-McAb Probe-Baed Rapid Immunoassay Strip for Simultaneous Detection of Fumonisins in Maize", J Sci Food Agric., Vo. 97, Oct. 27, 2016, pp. 2223-2229.

Qu, Qiaoyu, "Study on the Immunoassay Technology for N-methylcarbamate Insecticide Carbaryl and Carbofuran Pesticide Residue", China Master's Theses Full-Text Database, Agriculture Science and Technology No. 11, Nov. 15, 2014, China.

State Intellectual Property Office of People's Republic of China, "International Search Report for PCT Application No. PCT/CN2018/078198", China, Apr. 29, 2018.

* cited by examiner

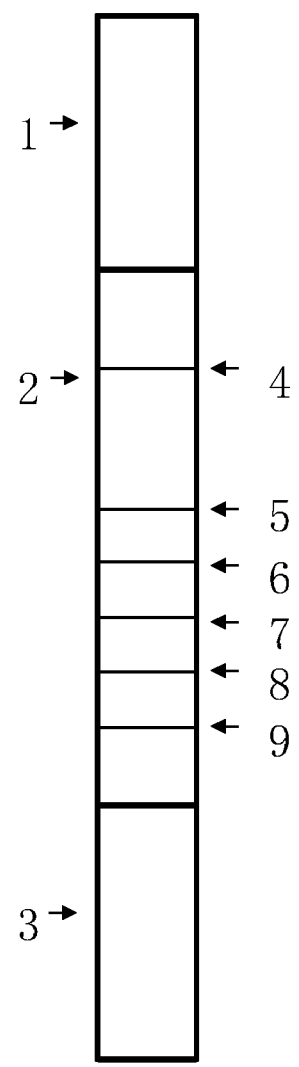

TIME-RESOLVED FLUORESCENCE IMMUNOCHROMATOGRAPHIC KIT FOR SIMULTANEOUS DETECTION OF MIXED CONTAMINATION OF FIVE MYCOTOXINS SUCH AS AFLATOXIN B1 AND APPLICATION THEREOF

SEQUENCE LISTING

This application includes a Sequence Listing in the ASCII text file in .txt format that is electronically submitted via EFS-Web on Nov. 16, 2020. The ASCII text file contains a sequence listing entitled "0123389180US9SequenceListing.txt" created on Nov. 16, 2020 and is 3,790 bytes in size. The Sequence Listing contained in this 0123389180US9SequenceListing.txt file is part of the specification and is hereby incorporated by reference herein in its entirety.

TECHNICAL FIELD

The invention relates to immunochromatographic time-resolved fluorescence kits for fungal toxins and particularly relates to an immunochromatographic time-resolved fluorescence kit for simultaneously detecting mixed pollution of five kinds of fungal toxins such as aflatoxin B1 and an application.

BACKGROUND

Fungal toxins are a series of hazardous and noxious substances generated from growth and metabolism of fungi in cereals & oils or feedstuffs, and the quantity of varieties of the fungal toxins discovered in the natural world at present is up to more than 400. According to main toxin producing strains, the fungal toxins can be classified into aspergillus toxins (such as aflatoxin and sterigmatocystin), penicillium toxins and fusarium toxins (such as zearalenone). The fungal toxins have carcinogenic, teratogenic and mutagenic effects, may cause acute or chronic poisoning of human bodies and severely impair human body health. The fungal toxins pollute crops, foodstuffs and feedstuffs and bring great threats to lives and health of human and domestic animals. In order to guarantee health and safety of the cereals, related limit standards (GB 2761-2011) for the fungal toxins in the cereals are established in our country. At present, main fungal toxins polluting agricultural product foodstuffs, feedstuffs, etc. comprise aflatoxin B1, fumonisin B1, ochratoxin A, zearalenone and sterigmatocystin. Aflatoxin mainly presents in cereals and leguminous plants, and the aflatoxin is detected in milk, dairy products, eggs and meat if poultry are in contact with aflatoxin polluted feedstuffs. The Aflatoxin is mainly infected through food digestion, and long-term skin contact also causes chronic infection, causes acute or chronic liver damage, acute hepatitis and hepatic cell steatosis and finally causes hepatic carcinoma. Fumonisin is a water-soluble metabolic product generated from Fusarium moniliforme, a di-ester compound mainly consisting of polyhydric alcohol and tricarballylic acid; at present, 11 kinds of fumonisin have already been discovered, in which fumonisin B1 is the most serious in damage and mainly infects crops such as corn, sorghum and rice. The fumonisin is a carcinogenic agent, causes hydrocephalus, brain necrosis and liver poisoning and seriously injures an immune system. Ochratoxin mainly infects cereal crops and leguminous plants, such as corn, barley, wheat, coffee beans, peas and cocoa beans. The ochratoxin has powerful renal toxicity in case of being absorbed by in-vivo gastro-intestinal tracts such as duodenums and jejunum sections. Zearalenone is widespread in pollution, can be detected in cereals and agricultural and subsidiary products of all continents in the world and mainly pollutes agricultural product foodstuffs such as corn, oats, wheat, barley and millet and foodstuffs such as dairy products and beeves. Sterigmatocystin is mainly a secondary metabolic product generated from fungi such as aspergillus flavus, aspergillus versicolor, aspergillus nidulans and aspergillus rugulosus, the toxicity of the sterigmatocystin is next only to that of the aflatoxin, and the sterigmatocystin can induce hepatic carcinoma, lung cancer and other tumors.

At present, detection methods of the fungal toxins mainly comprise thin-layer chromatography, enzyme-linked immunosorbent assay, liquid phase chromatography and liquid chromatography-mass spectrometer. The thin-layer chromatography is simple and convenient, but is poor in recurrence and low in accuracy; the enzyme-linked immunosorbent assay is high in specificity and simple in pretreatment, but is high in false positive rate, thereby being incapable of serving as a confirmatory method; and the liquid phase chromatography and the liquid chromatography-mass spectrometer are good in stability and relatively high in sensitivity, however, a sample pretreatment process is complicated, the detecting time is long, employed instruments are expensive, the requirements on experiment environments and detecting personnel are high, and rapid detecting is difficult to achieve. An immunochromatography fluorescence testing technology is an immunoassay method developed in early 1980s and is a rapid testing technology developed on the basis of a monoclonal antibody technology, a fluorescence labeling immunization technology and a new material technology. According to the technology, a microporous membrane serves as a solid phase carrier, and a known specific antigen is fixed onto a cellulose nitrate film as a test line. After a sample to be detected is added, the sample is combined with an immunoprobe firstly through diffusion of capillaries and is continuously subjected to chromatography to the test line, a complex of a labeled substance and a substance to be detected is intercepted by an antigen of the test line, and thus, a fluorescence ribbon is present. The method has the advantages of rapidness, high sensitivity, high specificity, good stability, simplicity in operation, etc., is direct-viewing and reliable in result judgment, is easily mastered by personnel of basic units, is applicable to on-scene rapid screening and basic unit large-area popularization and is particularly suitable for serving as a testing technology capable of rapidly and simultaneouslytesting fungal toxin mixed pollution desiderative to the fields of agricultural product foodstuffs and feedstuffs, thereby achieving simultaneous and rapid monitoring on mixed pollution of the fungal toxins in the agricultural product foodstuffs and feedstuffs.

SUMMARY

In view of the above problems, the present invention provides an immunochromatographic time-resolved fluorescence kit for simultaneously detecting mixed pollution of aflatoxin B1, fumonisin B1, ochratoxin A, zearalenone and sterigmatocystin, a preparation method and an application of the immunochromatographic time-resolved fluorescence kit. The immunochromatographic time-resolved fluorescence kit can be applied to simultaneous detection on the contents of the aflatoxin B1, the fumonisin B1, the ochratoxin A, the zearalenone and the sterigmatocystin and has the characteristics of being simple and rapid in operation and high in sensitivity.

In order to solve the above-mentioned technical problem, the present disclosure employs a technical scheme as follows:

An immunochromatographic time-resolved fluorescence kit for simultaneously detecting mixed pollution of aflatoxin B1, fumonisin B1, ochratoxin A, zearalenone and sterigmatocystin comprises an immunochromatographic time-resolved fluorescence test strip and a sample reaction bulb containing an europium-labeled aflatoxin B1 monoclonal antibody freeze-dried product, an europium-labeled fumonisin B1 monoclonal antibody freeze-dried product, an europium-labeled ochratoxin A monoclonal antibody freeze-dried product, an europium-labeled zearalenone monoclonal antibody freeze-dried product and an europium-labeled sterigmatocystin monoclonal antibody freeze-dried product. Wherein: the immunochromatographic time-resolved fluorescence test strip comprises a PVC substrate, an absorbent pad, a test pad and a sample pad are sequentially stuck to one face of the substrate from top to bottom, all the adjacent pads are in overlapped connection at joints, the test pad employs a cellulose nitrate film as a base pad, a transverse quality control line and 5 test lines are arranged on the cellulose nitrate film from top to bottom, the quality control line is coated with a rabbit antimouse polyclonal antibody, the 5 test lines are separately coated with an aflatoxin B1-bovine serum albumin conjugate, a fumonisin B1-bovine serum albumin conjugate, an ochratoxin A-bovine serum albumin conjugate, a zearalenone-bovine serum albumin conjugate and a sterigmatocystin-bovine serum albumin conjugate, and a monoclonal antibody of the fumonisin B1 is secreted from a hybridoma cell line Fm7A11 with an accession number of CCTCC NO. C201636. The hybridoma cell line Fm7A11 was stored/deposited under the terms of the Budapest Treaty in CCTCC (the China Center for Type Culture Collection) in Wuhan University, Wuhan, China, one of recognized International Depository Authorities (IDAs), on Mar. 29, 2016 and has an accession number of CCTCC NO: C201636. The hybridoma cell line Fm7A11 will be irrevocably and without restriction or condition released to the public upon the issuance of a patent would satisfy the deposit requirement made herein.

According to the above-mentioned scheme, europium-labeled monoclonal antibodies are prepared according to the following methods:

An europium-labeled aflatoxin B1 monoclonal antibody: a target product, i.e., the europium-labeled aflatoxin B1 monoclonal antibody is obtained through the steps of subjecting an aflatoxin B1 monoclonal antibody and an activated europium labeling reagent to mix and proceed an oscillatory reaction in a boric acid buffer solution, and then performing centrifuging, redissolving and sealing, wherein 30 μg to 80 μg of the aflatoxin B1 monoclonal antibody can be coupled by 1 mL of the activated europium labeling reagent.

An europium-labeled ochratoxin A monoclonal antibody: a target product, i.e., the europium-labeled ochratoxin A monoclonal antibody is obtained through the steps of subjecting an ochratoxin A monoclonal antibody and an activated europium labeling reagent to mix and proceed an oscillatory reaction in a boric acid buffer solution, and then performing centrifuging, redissolving and sealing, wherein 40 μg to 90 μg of the ochratoxin A monoclonal antibody can be coupled by 1 mL of the activated europium labeling reagent.

An europium-labeled zearalenone monoclonal antibody: a target product, i.e., the europium-labeled zearalenone monoclonal antibody is obtained through the steps of subjecting a zearalenone monoclonal antibody and an activated europium labeling reagent to dissolving and proceed an oscillatory reaction in a boric acid buffer solution, and then performing centrifuging, redissolving and sealing, wherein 30 μg to 90 μg of the zearalenone monoclonal antibody can be coupled by 1 mL of the activated europium labeling reagent.

An europium-labeled fumonisin B1 monoclonal antibody: a target product, i.e., the europium-labeled fumonisin B1 monoclonal antibody is obtained through the steps of subjecting a fumonisin B1 monoclonal antibody and an activated europium labeling reagent to dissolving and proceed an oscillatory reaction in a boric acid buffer solution, and then performing centrifuging, redissolving and sealing, wherein 30 μg to 80 μg of the fumonisin B1 monoclonal antibody can be coupled by 1 mL of the activated europium labeling reagent.

An europium-labeled sterigmatocystin monoclonal antibody: a target product, i.e., the europium-labeled sterigmatocystin monoclonal antibody is obtained through the steps of subjecting a sterigmatocystin monoclonal antibody and an activated europium labeling reagent to dissolving and proceed an oscillatory reaction in a boric acid buffer solution, and then performing centrifuging, redissolving and sealing, wherein 30 μg to 80 μg of the sterigmatocystin monoclonal antibody can be coupled by 1 mL of the activated europium labeling reagent.

According to the above-mentioned scheme, an activation method of the europium labeling reagent comprises the steps: taking the europium labeling reagent, subjecting the europium labeling reagent to ultrasonic dispersion in a 0.2 mol/L boric acid buffer solution with a pH of 8.2, then, slowly adding a carbodiimide solution, performing oscillating activation at room temperature, performing centrifuging to remove supernatant, and performing redissolving by using a 0.2 mol/L boric acid buffer solution with a pH of 8.2 for later use, wherein the activation time is 15-30 min.

According to the above-mentioned scheme, each of the prepared europium-labeled Aflatoxin B1 monoclonal antibody, the europium-labeled Fumonisin B1 monoclonal antibody, the europium-labeled Ochratoxin A monoclonal antibody, the europium-labeled Zearalenone monoclonal antibody and the europium-labeled Sterigmatocystin monoclonal antibody is redissolved into a 0.01 mol/L phosphoric acid buffer solution with a pH of 8.2 and containing 1.5% (m/v) of trehalose and 2% (m/v) of bovine serum albumin for later use; and when in use, the prepared solutions are placed in sample reaction bulbs and are freeze-dried in a freeze dryer, thereby obtaining each europium-labeled monoclonal antibody freeze-dried product for later use.

According to the above-mentioned scheme, in the immunochromatographic time-resolved fluorescence test strip, the absorbent pad has a length of 10-16 mm and a width of 3-5 mm; the test pad has a length of 25-33 mm and a width of 3-5 mm; the sample pad has a length of 12-18 mm and a width of 3-5 mm, and an overlapped length among all the adjacent pads is 1-2 mm; a spacing between the test line, close to the quality control line, on the test pad of the immunochromatographic time-resolved fluorescence test strip and the upper edge of the cellulose nitrate film is 5-10 mm, a spacing between every two adjacent test lines is 1.5-4.5 mm, and a spacing between the test line close to the quality control line and the quality control line is 3-6 mm; and the sample reaction bulb is a 1-5 mL bayonet bottle.

According to the above-mentioned scheme, a test line per centimeter on the test pad of the immunochromatographic time-resolved fluorescence test strip is coated with 100-400 ng of the aflatoxin B1-bovine serum albumin conjugate, a test line per centimeter is coated with 100-400 ng of the fumonisin B1-bovine serum albumin conjugate, a test line per centimeter is coated with 100-400 ng of the ochratoxin A-bovine serum albumin conjugate, a test line per centimeter is coated with 100-400 ng of the zearalenone-bovine serum albumin conjugate, and a test line per centimeter is coated with 100-400 ng of the sterigmatocystin-bovine serum albumin conjugate; and the quality control line per centimeter is coated with 80-200 ng of the rabbit antimouse polyclonal antibody.

The content of the europium-labeled aflatoxin B1 monoclonal antibody freeze-dried product in the sample reaction bulb is 0.1-0.3 μg the content of the europium-labeled fumonisin B1 monoclonal antibody freeze-dried product in the sample reaction bulb is 0.1-0.3 μg the content of the europium-labeled ochratoxin A monoclonal antibody freeze-dried product in the sample reaction bulb is 0.1-0.3 μg the content of the europium-labeled zearalenone monoclonal antibody freeze-dried product in the sample reaction bulb is 0.1-0.3 μg and the content of the europium-labeled sterigmatocystin monoclonal antibody freeze-dried product in the sample reaction bulb is 0.1-0.3 μg.

According to the above-mentioned scheme, the immunochromatographic time-resolved fluorescence kit for simultaneously detecting mixed pollution of aflatoxin B1, fumonisin B1, ochratoxin A, zearalenone and sterigmatocystin further comprises a sample diluent and a sample diluent suction pipe, and the sample diluent is a TWEEN® 20 aqueous solution with a volume percent of 0.01%-0.30%.

According to the above-mentioned scheme, a preparation method of the time-resolved fluorescence test strip comprises the steps as follows:

(1) Tailoring absorbent paper to obtain the absorbent pad;

(2) Preparation of the test pad:

Preparing 0.08-0.50 mg/mL coating solutions from the aflatoxin B1-bovine serum albumin conjugate, the fumonisin B1-bovine serum albumin conjugate, the ochratoxin A-bovine serum albumin conjugate, the zearalenone-bovine serum albumin conjugate and the sterigmatocystin-bovine serum albumin conjugate separately, coating the cellulose nitrate film separately with the coating solutions at intervals in a line spraying manner to obtain 5 test lines, and then, performing drying for 60-120 min at a temperature of 37-40° C.; and Preparing a 0.1-0.5 mg/mL coating solution from the rabbit antimouse polyclonal antibody, transversely coating the cellulose nitrate film with the coating solution in a line spraying manner to obtain a quality control line, and performing drying for 60-120 min at a temperature of 37-40° C.;

(3) Preparation of the sample pad:

Steeping a glass fiber film in sealing fluid, taking out the steeped glass fiber film, drying the glass fiber film for 4-6 h at a temperature of 37-40° C. to obtain a sample pad, and then, putting the sample pad into a dryer for room-temperature preservation; and (4) assembling of the immunochromatographic time-resolved fluorescence test strip:

Sticking the absorbent pad, the test pad and the sample pad to one face of the PVC substrate sequentially from top to bottom in a manner that all the adjacent pads are in overlapped connection at joints, thereby obtaining the immunochromatographic time-resolved fluorescence test strip.

According to the above-mentioned scheme, a coating buffer solution per 10 mL employed for preparing each of the aflatoxin B1-bovine serum albumin conjugate coating solution, the fumonisin B1-bovine serum albumin conjugate coating solution, the ochratoxin A-bovine serum albumin conjugate coating solution, the zearalenone-bovine serum albumin conjugate coating solution and the sterigmatocystin-bovine serum albumin conjugate coating solution during the preparation of the immunochromatographic time-resolved fluorescence test strip contains 0.1 g of bovine serum albumin, 0.002 g of sodium azide, 0.08 g of sodium chloride, 0.029 g of disodium hydrogen phosphate dodecahydrate, 0.002 g of potassium chloride and 0.002 g of potassium dihydrogen phosphate;

A coating buffer solution per 10 mL employed for preparing the rabbit antimouse polyclonal antibody coating solution contains 0.002 g of sodium azide, 0.08 g of sodium chloride, 0.029 g of disodium hydrogen phosphate dodecahydrate, 0.002 g of potassium chloride and 0.002 g of potassium dihydrogen phosphate; and The sealing fluid per 100 mL employed during the preparation of the immunochromatographic time-resolved fluorescence test strip contains 0.5 g of ovalbumin, 2 g of saccharose, 0.02 g of sodium azide, 0.8 g of sodium chloride, 0.29 g of disodium hydrogen phosphate dodecahydrate, 0.02 g of potassium chloride and 0.02 g of potassium dihydrogen phosphate.

Application of the immunochromatographic time-resolved fluorescence kit in detection on the contents of aflatoxin B1, fumonisin B1, ochratoxin A, zearalenone and sterigmatocystin: pretreating a sample to be detected to obtain a solution of the sample to be detected, adding the solution of the sample to be detected into a sample reaction bulb, performing uniform mixing, inserting the time-resolved fluorescence test strip, performing a reaction for 6-10 min at a temperature of 37° C., and then, performing testing by a time-resolved fluorescence tester to obtain a ratio of fluorescence intensity of each test line (T) to fluorescence intensity of the quality control line (C) on the immunochromatographic time-resolved fluorescence test strip; and obtaining the contents of the aflatoxin B1, the fumonisin B1, the ochratoxin A, the zearalenone and the sterigmatocystin in the solution of the sample to be detected on the basis of relationship curves between the ratio (T/C) of the fluorescence intensity of each test line to the fluorescence intensity of the quality control line of the immunochromatographic time-resolved fluorescence test strip and concentrations of the aflatoxin B1, the fumonisin B1, the ochratoxin A, the zearalenone and the sterigmatocystin, and finally, performing conversion, thereby obtaining the contents of the aflatoxin B1, the fumonisin B1, the ochratoxin A, the zearalenone and the sterigmatocystin in the sample to be detected.

According to the above-mentioned scheme, the relationship curves between the ratio (T/C) of the fluorescence intensity of each test line to the fluorescence intensity of the quality control line of the immunochromatographic time-resolved fluorescence test strip and the concentrations of the aflatoxin B1, the fumonisin B1, the ochratoxin A, the zearalenone and the sterigmatocystin are obtained by employing the following methods:

(1) Preparing standard solutions of the aflatoxin B1, the fumonisin B1, the ochratoxin A, the zearalenone and the sterigmatocystin of series gradient concentrations;

(2) Separately adding a proper volume of each of the standard solutions of the aflatoxin B1, the fumonisin B1, the ochratoxin A, the zearalenone and the sterigmatocystin of the gradient concentrations into the sample reaction bulb, performing uniform mixing, inserting immunochromatographic time-resolved fluorescence test strips, performing a reaction for 6 min at a temperature of 37° C., performing detecting with a time-resolved fluoroimmunoassay analyzer to obtain fluorescence intensities of a test line (T) and a quality control line (C) on each immunochromatographic time-resolved fluorescence test strip, thereby obtaining a ratio (T/C) of the fluorescence intensity of each test line to the fluorescence intensity of the quality control line of each immunochromatographic time-resolved fluorescence test strip; and (3) Performing fitting, thereby obtaining the relationship curves between the ratio (T/C) of the fluorescence intensity of each test line to the fluorescence intensity of the quality control line of the immunochromatographic time-resolved fluorescence test strip and the concentrations of the aflatoxin B1, the fumonisin B1, the ochratoxin A, the zearalenone and the sterigmatocystin.

The present disclosure has the beneficial effects that:

(1) The aflatoxin B1, fumonisin B1, ochratoxin A, zearalenone and sterigmatocystin are rapidly, simultaneously and quantitatively detected. The immunochromatographic time-resolved fluorescence kit provided by the present disclosure can be used for rapidly, simultaneously and quantitatively detecting the aflatoxin B1, the fumonisin B1, the ochratoxin A, the zearalenone and the sterigmatocystin on one test strip, all antibodies employed are monoclonal antibodies and are good in specificity and high in sensitivity, and detection among all fungal toxins is free of interference and is simple and rapid.

(2) The sensitivity is high. The immunochromatographic time-resolved fluorescence kit provided by the present disclosure has minimum detection limits of 0.06 ng/mL to the aflatoxin B1, 0.2 ng/mL to the fumonisin B1, 0.5 ng/mL to the ochratoxin A, 1 ng/mL to the zearalenone and 0.3 ng/mL to the sterigmatocystin in a detected solution, and the detection limits can meet requirements of European Union on limits to this 5 kinds of fungal toxins in foods.

BRIEF DESCRIPTION OF THE DRAWINGS

FIG. 1 is a structural schematic diagram of an immunochromatographic time-resolved fluorescence test strip of an immunochromatographic time-resolved fluorescence kit for aflatoxin B1, fumonisin B1, ochratoxin A, zearalenone and sterigmatocystin provided by the present disclosure. Wherein: 1 absorbent pad, 2 test pad, 3 sample pad, 4 quality control line, 5 aflatoxin B1 test line, 6 fumonisin B1 test line, 7 ochratoxin A test line, 8 zearalenone test line, and 9 sterigmatocystin test line.

DETAILED DESCRIPTION OF THE EMBODIMENTS

Embodiment 1 Obtaining of Aflatoxin B1 Monoclonal Antibody

A general monoclonal antibody of aflatoxin is secreted from a hybridoma cell line 3G1 with an accession number of CCTCC NO. C201014 and is particularly prepared in advance according to a method reported in a patent with patent number of ZL201210117614.9. The hybridoma cell line 3G1 was stored/deposited under the terms of the Budapest Treaty in CCTCC (the China Center for Type Culture Collection) in Wuhan University, Wuhan, China, one of recognized International Depository Authorities (IDAs), on Jul. 13, 2010 and has an accession number of CCTCC NO. C201014. The hybridoma cell line 3G1 will be irrevocably and without restriction or condition released to the public upon the issuance of a patent would satisfy the deposit requirement made herein. The preparation method comprises the steps: injecting the obtained hybridoma cell line 3G1 into BALB/c mice which are treated with a Freund's incomplete adjuvant in advance, collecting ascitic fluid from the mice, and performing purifying treatment, thereby obtaining the aflatoxin B1 monoclonal antibody. Wherein, a caprylic acid-ammonium sulfate method serves as a purification method and comprises the specific operations: filtering the ascitic fluid of the mice with double-layer filter paper, subjecting the filtered ascitic fluid to centrifuging for 15 min or more at a temperature of 4° C. and a rate of revolution of 12,000 r/min, sucking the obtained supernatant, mixing the supernatant with an acetate buffer solution, of which the volume is 4 times that of the supernatant, slowly adding n-caprylic acid with stirring in accordance with that the ascitic fluid per milliliter needs 30-35 λL of n-caprylic acid, performing room-temperature mixing for 30-60 min, performing standing for 2 h or more at a temperature of 4° C., then, performing centrifuging for 30 min or more at a temperature of 4° C. and a rate of revolution of 12,000 r/min, discarding the obtained precipitate, filtering the obtained supernatant with double-layer filter paper, then, adding a phosphate buffer solution with a molar concentration of 0.1 mol/L and a pH value of 7.4, of which the volume is 1/10 that of the filter liquor, adjusting a pH value of the liquid mixture to 7.4 with a 2 mol/L sodium hydroxide solution, performing precooling at a temperature of 4° C., slowly adding ammonium sulfate until a final concentration of ammonium sulfate is 0.277 g/mL, performing standing for 2 h or more at a temperature of 4° C., then, performing centrifuging for 30 min or more at a temperature of 4° C. and a rate of revolution of 12,000 r/min, discarding the obtained supernatant, resuspending the obtained precipitate with a 0.01 mol/L phosphate buffer solution, of which the volume is 1/10 of the original ascitic fluid volume, loading the suspension to a dialysis bag, performing dialysis with pure water, freezing a sufficiently-dialyzed protein solution in a refrigerator with a temperature of −70° C., then, performing freeze-drying with a freezing vacuum dryer, collecting freeze-dried powder, i.e., purified aflatoxin B1 monoclonal antibody, and placing the antibody in a refrigerator with a temperature of −20° C. for later use; and The acetate buffer solution is obtained through adding water into 0.29 g of sodium acetate and 0.141 mL of acetic acid until a constant volume is 100 mL; and the 0.1 mol/L phosphate buffer solution is obtained through adding water to 0.8 g of sodium chloride, 0.29 g of disodium hydrogen phosphate dodecahydrate, 0.02 g of potassium chloride and 0.02 g of potassium dihydrogen phosphate until a constant volume is 100 mL.

Embodiment 2 Obtaining of Ochratoxin A Monoclonal Antibody

The ochratoxin A monoclonal antibody is secreted from a hybridoma cell line 1H2 with an accession number of CCTCC NO. C201329 and is particularly prepared in advance according to a method reported in a patent with an application number of 201310115921.8. The hybridoma cell line 1H2 was stored/deposited under the terms of the Budapest Treaty in CCTCC (the China Center for Type Culture Collection) in Wuhan University, Wuhan, China, one of recognized International Depository Authorities (IDAs), on Mar. 7, 2013 and has an accession number of CCTCC NO. C201329. The hybridoma cell line 1H2 will be irrevocably and without restriction or condition released to the public upon the issuance of a patent would satisfy the deposit requirement made herein. The preparation method comprises the steps: injecting the hybridoma cell line 1H2 into abdominal parts of BALB/c mice which are treated with a Freund's incomplete adjuvant in advance, collecting ascitic fluid from the mice, and performing purifying, thereby obtaining the ochratoxin A monoclonal antibody. A caprylic acid- ammonium sulfate method serves as a purification method and comprises the specific steps: filtering the ascitic fluid of the mice with double-layer filter paper, performing centrifuging for 15 min or more at a temperature of 4° C. and a rate of revolution of 12,000 r/min, sucking the obtained supernatant, mixing the obtained ascitic fluid supernatant with an acetate buffer solution, of which the volume is 4 times that of the supernatant, slowly adding n-caprylic acid with stirring in accordance with that the ascitic fluid per milliliter needs 30-35 μL of n-caprylic acid, performing room-temperature mixing for 30-60 min, performing standing for 2 h or more at a temperature of 4° C., then, performing centrifuging for 30 min or more at a temperature of 4° C. and a rate of revolution of 12,000 r/min, discarding the obtained precipitate, filtering the obtained supernatant with double-layer filter paper, then, adding a phosphate buffer solution with a molar concentration of 0.1 mol/L and a pH value of 7.4, of which the volume is 1/10 that of the filter liquor, adjusting a pH value of the liquid mixture to 7.4 with a 2 mol/L sodium hydroxide solution, performing precooling at a temperature of 4°° C., slowly adding ammonium sulfate until a final concentration of ammonium sulfate is 0.277 g/mL, performing standing for 2h or more at a temperature of 4° C., then, performing centrifuging for 30 min or more at a temperature of 4° C. and a rate of revolution of 12,000 r/min, discarding the obtained supernatant, resuspending the obtained precipitate with a 0.01 mol/L phosphate buffer solution with a pH value of 7.4, of which the volume is 1/10 of the original ascitic fluid volume, loading the suspension to a dialysis bag, performing dialysis with pure water, freezing a sufficiently-dialyzed protein solution in a refrigerator with a temperature of −70° C., then, performing freeze-drying with a freeze dryer, collecting freeze-dried powder, i.e., purified ochratoxin A monoclonal antibody, and placing the antibody in a refrigerator with a temperature of −20° C. for later use; and The acetate buffer solution is obtained through adding water into 0.29 g of sodium acetate and 0.141 mL of acetic acid until a constant volume is 100 mL; the 0.01 mol/L phosphate buffer solution is obtained through adding water to 0.8 g of sodium chloride, 0.29 g of disodium hydrogen phosphate dodecahydrate, 0.02 g of potassium chloride and 0.02 g of potassium dihydrogen phosphate until a constant volume is 100 mL; and the 0.1 mol/L phosphate buffer solution is obtained through adding water to 8 g of sodium chloride, 2.9 g of disodium hydrogen phosphate dodecahydrate, 0.2 g of potassium chloride and 0.2 g of potassium dihydrogen phosphate until a constant volume is 100 mL.

Embodiment 3 Obtaining of Zearalenone Monoclonal Antibody

The zearalenone monoclonal antibody is secreted from a hybridoma cell line 2D3 with an accession number of CCTCC NO. C201328 and is particularly prepared in advance according to a method reported in a patent with an application number of 201310115825.3. The hybridoma cell line 2D3 was stored/deposited under the terms of the Budapest Treaty in CCTCC (the China Center for Type Culture Collection) in Wuhan University, Wuhan, China, one of recognized International Depository Authorities (IDAs), on Mar. 7, 2013 and has an accession number of CCTCC NO. C201328. The hybridoma cell line 2D3 will be irrevocably and without restriction or condition released to the public upon the issuance of a patent would satisfy the deposit requirement made herein. The preparation method comprises the steps: injecting the hybridoma cell line 2D3 into abdominal parts of BALB/c mice which are treated with a Freund's incomplete adjuvant in advance, collecting ascitic fluid from the mice, and performing purifying, thereby obtaining the zearalenone monoclonal antibody. A caprylic acid-ammonium sulfate method serves as a purification method and comprises the specific steps: filtering the ascitic fluid of the mice with double-layer filter paper, performing centrifuging for 15 min or more at a temperature of 4° C. and a rate of revolution of 12,000 r/min, sucking the obtained supernatant, mixing the obtained ascitic fluid supernatant with an acetate buffer solution, of which the volume is 4 times that of the supernatant, slowly adding n-caprylic acid with stirring in accordance with that the ascitic fluid per milliliter needs 30-35 μL of n-caprylic acid, performing room-temperature mixing for 30-60 min, performing standing for 2 h or more at a temperature of 4° C., then, performing centrifuging for 30 min or more at a temperature of 4° C. and a rate of revolution of 12,000 r/min, discarding the obtained precipitate, filtering the obtained supernatant with double-layer filter paper, then, adding a phosphate buffer solution with a molar concentration of 0.1 mol/L and a pH value of 7.4, of which the volume is 1/10 that of the filter liquor, adjusting a pH value of the liquid mixture to 7.4 with a 2 mol/L sodium hydroxide solution, performing precooling at a temperature of 4° C., slowly adding ammonium sulfate until a final concentration of ammonium sulfate is 0.277 g/mL, performing standing for 2 h or more at a temperature of 4° C., then, performing centrifuging for 30 min or more at a temperature of 4° C. and a rate of revolution of 12,000 r/min, discarding the obtained supernatant, resuspending the obtained precipitate with a 0.01 mol/L phosphate buffer solution with a pH value of 7.4, of which the volume is 1/10 of the original ascitic fluid volume, loading the suspension to a dialysis bag, performing dialysis with pure water, freezing a sufficiently-dialyzed protein solution in a refrigerator with a temperature of −70°° C., then, performing freeze-drying with a freeze dryer, collecting freeze-dried powder, i.e., purified zearalenone monoclonal antibody, and placing the antibody in a refrigerator with a temperature of −20° C. for later use; and The acetate buffer solution is obtained through adding water into 0.29 g of sodium acetate and 0.141 mL of acetic acid until a constant volume is 100 mL; the 0.01 mol/L phosphate buffer solution is obtained through adding water to 0.8 g of sodium chloride, 0.29 g of disodium hydrogen phosphate dodecahydrate, 0.02 g of potassium chloride and 0.02 g of potassium dihydrogen phosphate until a constant volume is 100 mL; and The 0.1 mol/L phosphate buffer solution is obtained through adding water to 8 g of sodium

Embodiment 4 Obtaining of Sterigmatocystin Monoclonal Antibody

The sterigmatocystin monoclonal antibody is secreted from a hybridoma cell line ST03 with an accession number of CCTCC NO. C2013187 and is particularly prepared in advance according to a method reported in a patent with an application number of 201410115952.8. The hybridoma cell line ST03 was stored/deposited under the terms of the Budapest Treaty in CCTCC (the China Center for Type Culture Collection) in Wuhan University, Wuhan, China, one of recognized International Depository Authorities (IDAs), on Nov. 13, 2013 and has an accession number of CCTCC NO. C2013187. The hybridoma cell line ST03 will be irrevocably and without restriction or condition released to the public upon the issuance of a patent would satisfy the deposit requirement made herein. The preparation method comprises the steps: injecting the obtained hybridoma cell line ST03 into abdominal parts of Balb/c mice which are treated with a Freund's incomplete adjuvant in advance, collecting ascitic fluid from the mice, and performing purifying, thereby obtaining the sterigmatocystin monoclonal antibody. A caprylic acid-ammonium sulfate purification method serves as a purification method and comprises the specific operations: filtering the ascitic fluid of the mice with double-layer filter paper, performing centrifuging for 15 min or more at a temperature of 4° C. and a rate of revolution of 12,000 r/min, sucking the obtained supernatant, mixing the obtained ascitic fluid supernatant with an acetate buffer solution, of which the volume is 4 times that of the supernatant, slowly adding n-caprylic acid with stirring in accordance with that the ascitic fluid per milliliter needs 33 µL of n-caprylic acid, performing room-temperature mixing for 30-60 min, performing standing for 2 h or more at a temperature of 4° C., then, performing centrifuging for 30 min or more at a temperature of 4° C. and a rate of revolution of 12,000 r/min, discarding the obtained precipitate, filtering the obtained supernatant with double-layer filter paper, then, adding a phosphate buffer solution with a molar concentration of 0.1 mol/L and a pH value of 7.4, of which the volume is 1/10 that of the filter liquor, adjusting a pH value of the liquid mixture to 7.4 with a 2 mol/L sodium hydroxide solution, performing precooling at a temperature of 4° C., slowly adding ammonium sulfate until a final concentration of ammonium sulfate is 0.277 g/mL, performing standing for 2 h or more at a temperature of 420 C., then, performing centrifuging for 30 min or more at a temperature of 4° C. and a rate of revolution of 12,000 r/min, discarding the obtained supernatant, resuspending the obtained precipitate with a 0.01 mol/L phosphate buffer solution, of which the volume is 1/10 of the original ascitic fluid volume, loading the suspension to a dialysis bag, performing dialysis with pure water, freezing a sufficiently-dialyzed protein solution in a refrigerator with a temperature of −70° C., then, performing freeze-drying with a freeze dryer, collecting freeze-dried powder, i.e., purified sterigmatocystin monoclonal antibody, and placing the antibody in a refrigerator with a temperature of −20° C. for later use; and The acetate buffer solution is obtained through adding water into 0.29 g of sodium acetate and 0.141 mL of acetic acid until a constant volume is 100 mL; and the 0.1 mol/L phosphate buffer solution is obtained through adding water to 0.8 g of sodium chloride, 0.29 g of disodium hydrogen chloride, 2.9 g of disodium hydrogen phosphate dodecahydrate, 0.2 g of potassium chloride and 0.2 g of potassium dihydrogen phosphate until a constant volume is 100 mL.

Embodiment 5 Obtaining of Fumonisin B1 Monoclonal Antibody

Screening of Hybridoma Cell Line Fm7A11
1. Antigen Synthesis and Animal Immunization A complete antigen is synthesized from a purchased commercially available fumonisin B1 standard substance through specific synthesis steps as follows: 2 mg of FB1 standard substance powder and 2 mg of EDC are dissolved into 500 µL of 0.01 mol/L PBS solution separately to obtain an EDC solution and a FB1 solution, 4 mg/mL of EDC solution (0.01 mol/L PBS solution) is dropwise added into the dissolved FB1 solution, and gentle stirring is performed for 10 minutes at room temperature. 5 mg/mL (0.01 mol/L PBS solution) BSA solution is dropwise added into the above-mentioned liquid mixture, and a reaction is performed for 4 hours with stirring at room temperature. Dialysis is performed for 3 days. Finally, conventional ultraviolet scanning-method identification is performed, and an identification result shows that a FB1-BSA complete antigen is successfully prepared.

6 BALB/c mice of 6 weeks old and a fumonisin complete antigen FB1-BSA synthesized in an immunization laboratory are purchased. During first-time immunization, the fumonisin complete antigen and an isovolumetric Freund's complete adjuvant are emulsified and then are injected to multiple subcutaneous points of napes of the mice. Second-time immunization is performed 3 weeks later, a Freund's incomplete adjuvant and the isovolumetric fumonisin complete antigen are emulsified and are injected to multiple subcutaneous points of napes of the mice. Third-time immunization and fourth-time immunization are performed at intervals of 2 weeks from last time of immunization and have the same immunization mode as that of the second-time immunization. Four times of immunization are the same in dose and are only 100 µg per mouse. On 7th day after the third-time immunization, blood is extracted from caudal veins of the mice, serum is separated, the titer of the serum of the mice is monitored by adopting an indirect ELISA method, the sensitivity of the serum of the mice is assayed by an indirect competitive ELISA method, the mice corresponding to the serum with relatively high titer and sensitivity are selected and are subjected to last-time reinforced immunization, and the immunizing dose is doubled to a former dose.

2. Cell Fusion 3 days after last-time reinforced immunization, a 50% (weight percent) polyethylene glycol, i.e., PEG (molecular weight: 1,450) is adopted as a fusion agent, and cell fusion is performed according to a conventional method and comprises the specific steps: killing the mice to be subjected to fusion under aseptic conditions by cervical dislocation, separating spleen cells, mixing the spleen cells with mouse-sourced myeloma cells SP2/0 according to a number ratio of 5:1, washing the mixed cells with RPMI-1640 basic culture fluid, and performing centrifuging for 5 min at a rate of revolution of 1,200 rpm. Discarding the obtained supernatant, draining, adding 1 mL of PEG, performing fusing for 1 min, slowly adding RPMI-1640 basic culture fluid, performing centrifuging, discarding the obtained supernatant to obtain a precipitate, i.e., fused cells, resuspending the fused cells with 20 mL of complete medium, adding suspended cells into 80 mL of semisolid medium, performing uniform mixing, then, adding the mixture onto a 6-well cell culture plate by 2 mL/well, and performing culture in a carbon dioxide incubator with a temperature of 37° C.

The cell complete medium containing 1% of HAT contains 20% (volume percent) of fetal calf serum, 75% (volume percent) of RPMI-1640 basic culture fluid, 1% (weight percent) of L-glutamine, 1% (volume percent) of HEPES, 1% (volume percent) of double-antibody (10,000 unit per milliliter of penicillin and 10,000 mg per milliliter of streptomycin), 2% (volume percent) of growth factor (HFCS) and 1% (weight percent) of hypoxanthine-aminopterin-thymidine, i.e., HAT, and methylcellulose which are purchased from sigma-Aldrich.

3. Screening and Cloning of Cell Lines

In 2-3 weeks after cell fusion, when a cell colony grows until the cell colony is apparent to naked eyes, clones are picked up from a culture medium with a micropipettor and are transferred to a 96-well cell culture plate, liquid culture is performed by adopting HAT, and cultured supernatant is sucked for detection when cells grow to 2/3 of well bottoms. A two-step screening method is employed, and an indirect ELISA method is adopted in a first step to screen out positive wells, which are resistant to fumonisin and not resistant to carrier protein BSA; and an indirect competitive ELISA method is employed in a second step to detect the positive wells screened out in the first step, fumonisin B1 serves as a competitive antigen, wells (relatively high light absorption values mean that final measured values of wells with the competitive antigen of 0, i.e., positive control wells are relatively high, and relatively high sensitivity means that a concentration of the competitive antigen, i.e., an IC50 value is relatively low when a suppression ratio is 50%) with relatively high light absorption value and sensitivity are selected, subcloning is performed by employing a limited dilution method, the same two-step method is adopted for detection after subcloning, and subcloning is repeated to be performed for 4-5 times in such a manner to obtain a hybridoma cell line Fm7A11. The hybridoma cell line Fm7A11 was stored/deposited under the terms of the Budapest Treaty in CCTCC in Wuhan University, Wuhan, China on Mar. 29, 2016 and has an accession number of CCTCC NO: C201636.

Sequencing of variable region of antibody of hybridoma cell line Fm7A11 of fumonisin B1 monoclonal antibody (1) Extraction of total RNA: extracting total RNA capable of generating the hybridoma cell line Fm7A11 according to a description by employing a total RNA extracting kit of TianGen company;

(2) Synthesis of cDNA: performing reverse transcription by taking the total RNA obtained in the step 1 as a template and taking oligo(dT)15 as a primer according to a description of a reverse transcriptase SuperScript™-2II to synthesize a first chain of cDNA, wherein the primer oligo(dT)15 is purchased from Invitrogen; and (3) PCR-method cloning of variable region genes: designing primers according to conserved sites of a gene sequence of a mouse antibody in GENBANK, and amplifying the variable region genes of heavy and light chains of the antibody by taking the cDNA as a template. PCR program: performing amplification for 30 cycles according to 94° C. 30 s, 58° C. 45 s and 72° C. 1 min, and finally, performing extension for 10 min at a temperature of 72° C. After a PCR product is subjected to electrophoretic separation through 1% (weight percent) of sepharose, DNA fragments are purified and recovered by a kit and are connected into a vector pMD18-T, DH5α competence cells of *Escherichia coli* are converted, and positive clones are picked and are delivered to Shanghai Sunny Biotech Co., Ltd. for sequencing. Wherein, sequences of the primers are separately as follows: heavy chain variable region primers are 5'-CAG GTS MAR CTG MAG GAG TCW G-3'(22mer) and 5'-CAG GGG CCA GTG GAT AGA CAG ATG GGG G-3'(28mer), wherein S, M, R and W are Merger basic groups, M=A/C, R=A/G, S=G/C, W=A/T; and light chain variable region primers are 5'-GAC ATC AAG ATG ACC CAG TCT CCA-3'(24mer) and 5'-CCG TTT TAT TTC CAG CTT GGT CCC-3'(24mer).

An obtained gene sequence result: a heavy chain variable region coded gene sequence has a length of 379 bp and is shown in SEQ ID NO: 1, the condition that a heavy chain variable region coded by the gene sequence is composed of 126 amino acids is deduced according to the obtained gene sequence, and the sequence is shown in SEQ ID NO: 3. A light chain variable region coded gene sequence has a length of 348 bp and is shown in SEQ ID NO: 2, the condition that a light chain variable region coded by the gene sequence is composed of 116 amino acids is deduced according to the obtained gene sequence, and the sequence is shown in SEQ ID NO: 4.

5. Preparation Purification of Fumonisin B1 Monoclonal Antibody, Subtype and Characteristic Identification BALB/c mice, which are treated with a Freund's incomplete adjuvant in advance, are injected with the hybridoma cell line Fm7A11 of the fumonisin B1 monoclonal antibody obtained in the embodiment 1, ascitic fluid of the mice is collected, the antibody is purified by employing a caprylic acid-ammonium sulfate method, and specific operations are as follows: filtering the ascitic fluid of the mice with double-layer filter paper, subjecting the filtered ascitic fluid to centrifuging for 15 min or more at a temperature of 4° C. and a rate of revolution of 12,000 r/min, sucking the obtained supernatant, mixing the obtained ascitic fluid supernatant with an acetate buffer solution, of which the volume is 4 times that of the supernatant, slowly adding n-caprylic acid with stirring in accordance with that the ascitic fluid per milliliter needs 30-35 μL of n-caprylic acid, performing room-temperature mixing for 30-60 min, performing standing for 2 h or more at a temperature of 4° C., performing centrifuging for 30 min or more at a temperature of 4° C. and a rate of revolution of 12,000 r/min, discarding the obtained precipitate, filtering the obtained supernatant with double-layer filter paper, then, adding a phosphate buffer solution with a molar concentration of 0.1 mol/L and a pH value of 7.4, of which the volume is 1/10 that of the filter liquor, adjusting a pH value of the liquid mixture to 7.4 with a 2 mol/L sodium hydroxide solution, slowly adding ammonium sulfate in an ice bath until a final concentration of ammonium sulfate is 0.277 g/mL, performing standing for 2 h or more at a temperature of 4° C., then, performing centrifuging for 30 min or more at a temperature of 4° C. and a rate of revolution of 12,000 r/min, discarding the obtained supernatant, resuspending the obtained precipitate with a 0.01 mol/L phosphate buffer solution with a pH value of 7.4, of which the volume is 1/10 of the original ascitic fluid volume, loading the suspension to a dialysis bag, performing dialysis with 0.01 mol/L PBS for two days, then, performing dialysis with PB for two days, taking out a protein solution from the dialysis bag, performing centrifuging, collecting the obtained supernatant, discarding the obtained precipitate, pre-freezing the supernatant at a temperature of −70° C., then, performing freeze-drying with a freeze dryer, collecting freeze-dried powder, i.e., purified fumonisin B1 monoclonal antibody;

The acetate buffer solution is obtained through adding water into 0.29 g of sodium acetate and 0.141 mL of acetic acid until a constant volume is 100 mL; the 0.01 mol/L phosphate buffer solution is obtained through adding water to 0.8 g of sodium chloride, 0.29 g of disodium hydrogen phosphate dodecahydrate, 0.02 g of potassium chloride and 0.02 g of potassium dihydrogen phosphate until a constant volume is 100 mL; and the 0.1 mol/L phosphate buffer solution is obtained through adding water to 8 g of sodium chloride, 2.9 g of disodium hydrogen phosphate dodecahydrate, 0.2 g of potassium chloride and 0.2 g of potassium dihydrogen phosphate until a constant volume is 100 mL.

A subtype of the fumonisin B1 monoclonal antibody secreted from the hybridoma cell line Fm7A11 is identified as IgG2b by a commercially available subtype identification kit.

The condition that the titer of the antibody obtained through purifying the ascitic fluid of the mice can reach $3.2 \times 10^5$ is assayed by a conventional noncompetitive enzyme-linked immunosorbent assay (ELISA), i.e., a solution assayed result is positive when the antibody is diluted by $3.2 \times 10^5$ times. Assayed by conventional indirect competitive ELISA, the sensitivity to fumonisin B1 is 0.32 ng/mL. Cross rates of response to fumonisin B2 and B3 are 4.3% and 12.8%. Cross rates of response to aflatoxin, zearalenone, T-2 toxin, ochratoxin and vomitoxin are all lower than 0.1%.

Embodiment 6

Europium fluorescence microspheres are taken and added into 1 mL of 0.2 mol/L boric acid buffer solution with a pH of 8.2, ultrasonic treatment is performed for 40 seconds at a power of 300 w, then, 40 μL of 15 mg/mL carbodiimide is slowly added, shaking is performed for 20 min at room temperature, then, centrifuging is performed for 15 min at 17,000 g, the obtained precipitate is collected, the precipitate is redissolved by a 0.2 mol/L boric acid buffer solution with a pH of 8.2, activated fluorescence microspheres are added into 1 mg/ml antibodies (35 μl of aflatoxin B1 monoclonal antibody, 45 μl of ochratoxin A monoclonal antibody, 55 μl of zearalenone monoclonal antibody, 40 μl of fumonisin B1 monoclonal antibody and 50 μl of sterigmatocystin monoclonal antibody), a reaction is carried out for 12 h with shaking and stirring at a temperature of 4° C., centrifuging is performed for 10 min at 12,000 g, redissolving is performed with a 0.2 mol/L boric acid buffer solution containing 1% BSA and with a pH of 8.2, a reaction is carried out for 4 h with shaking and stirring at a temperature of 4° C., centrifuging is performed for 10 min at 12,000 g, the obtained precipitate is collected, the collected precipitate is redissolved into a 0.2 mol/L boric acid buffer solution with a pH of 8.2 containing 1.5% (m/v) of trehalose and 2% (m/v) of bovine serum albumin to obtain an europium-labeled fungal toxin antibody, and the europium-labeled fungal toxin antibody is preserved at a temperature of 4° C. for later use.

An immunochromatographic time-resolved fluorescence kit for simultaneously detecting mixed pollution of aflatoxin B1, fumoni sin B1, ochratoxin A, zearalenone and sterigmatocystin and an application of the immunochromatographic time-resolved fluorescence kit The immunochromatographic time-resolved fluorescence kit for simultaneously detecting mixed pollution of aflatoxin B1, fumonisin B1, ochratoxin A, zearalenone and sterigmatocystin comprises an immunochromatographic time-resolved fluorescence test strip, a sample reaction bulb containing an europium-labeled aflatoxin B1 monoclonal antibody freeze-dried product, an europium-labeled fumonisin B1 monoclonal antibody freeze-dried product, an europium-labeled ochratoxin A monoclonal antibody freeze-dried product, an europium-labeled zearalenone monoclonal antibody freeze-dried product and an europium-labeled sterigmatocystin monoclonal antibody freeze-dried product, a sample diluent and a sample diluent suction pipe, wherein the immunochromatographic time-resolved fluorescence test strip comprises a PVC substrate, an absorbent pad, a test pad and a sample pad are sequentially stuck to one face of the PVC substrate from top to bottom, all the adjacent pads are in overlapped connection at joints, and an overlapped length is 1 mm;

(1) Preparation of the Absorbent Pad

Tailoring absorbent paper into a specification with a length of 16 mm and a width of 4 mm, thereby obtaining the absorbent pad;

(2) Preparation of the Test Pad

Coating of test lines:

Preparing a 0.25 mg/mL solution from an aflatoxin B1-bovine serum albumin conjugate by using a coating buffer solution, and coating a position, 6 mm away from the upper edge of a cellulose nitrate film, of a cellulose nitrate film with the solution in a line spraying manner to obtain a test line I, wherein the test line I per centimeter is coated with 100 ng of the aflatoxin B1-bovine serum albumin conjugate; preparing a 0.25 mg/mL coating solution from a fumonisin B1-bovine serum albumin conjugate by using a coating buffer solution, and coating a position, 4 mm away from the test line I, of the cellulose nitrate film with the coating solution in a line spraying manner to obtain a test line II, wherein the test line II per centimeter is coated with 200 ng of the fumonisin B1-bovine serum albumin conjugate; preparing a 0.45 mg/mL coating solution from an ochratoxin A-bovine serum albumin conjugate by using a coating buffer solution, and coating a position, 4 mm away from the test line II, of the cellulose nitrate film with the coating solution in a line spraying manner to obtain a test line III, wherein the test line III per centimeter is coated with 160 ng of the ochratoxin A-bovine serum albumin conjugate; preparing a 0.35 mg/mL coating solution from a zearalenone-bovine serum albumin conjugate by using a coating buffer solution, and coating a position, 4 mm away from the test line III, of the cellulose nitrate film with the coating solution in a line spraying manner to obtain a test line IV, wherein the test line IV per centimeter is coated with 200 ng of the zearalenone-bovine serum albumin conjugate; preparing a 0.4 mg/mL coating solution from a sterigmatocystin-bovine serum albumin conjugate by using a coating buffer solution, and coating a position, 4 mm away from the test line IV, of the cellulose nitrate film with the coating solution in a line spraying manner to obtain a test line V, wherein the test line V per centimeter is coated with 200 ng of the sterigmatocystin-bovine serum albumin conjugate; and then, performing drying for 120 min at a temperature of 37° C.;

Coating of a Quality Control Line

Preparing a 0.4 mg/mL coating solution from a rabbit antimouse polyclonal antibody with a coating buffer solution, transversely coating a position, 4.5 mm away from the test line I, of the cellulose nitrate film with the coating solution in a line spraying manner to obtain a quality control line, wherein the control quality line per centimeter is coated with 120 ng of the rabbit antimouse polyclonal antibody, and then, performing drying for 120 min at a temperature of 37° C.;

The coating buffer solution is prepared through adding water to 0.002 g of sodium azide, 0.08 g of sodium chloride, 0.029 g of disodium hydrogen phosphate dodecahydrate, 0.002 g of potassium chloride and 0.002 g of potassium dihydrogen phosphate until a constant volume is 10 mL; and The cellulose nitrate film has a length of 33 mm and a width of 4 mm.

(3) Preparation of the Sample Pad:

Tailoring a glass fiber film into a specification with a length of 12 mm and a width of 4 mm, steeping the tailored glass fiber film in sealing fluid, taking out the steeped glass fiber film, drying the glass fiber film for 4 h at a temperature of 40° C. to obtain the sample pad, and then, putting the sample pad into a dryer for room-temperature preservation; and The sealing fluid is prepared through adding water to 1 g of ovalbumin, 2 g of saccharose, 0.02 g of sodium azide, 0.8 g of sodium chloride, 0.29 g of disodium hydrogen phosphate dodecahydrate, 0.02 g of potassium chloride and 0.02 g of potassium dihydrogen phosphate until a constant volume is 100 mL; and (4) Assembling of the Immunochromatographic Time-Resolved Fluorescence Test Strip:

Sticking the absorbent pad, the test pad and the sample pad to one face of the PVC substrate sequentially from top to bottom in a manner that all the adjacent pads are in overlapped connection at joints and an overlapped length is 1 mm, thereby obtaining the immunochromatographic time-resolved fluorescence test strip, referring to FIG. 1;

Obtaining of the sample reaction bulb: redissolving each of the prepared europium-labeled aflatoxin B1 monoclonal antibody, the europium-labeled fumonisin B1 monoclonal antibody, the europium-labeled ochratoxin A monoclonal antibody, the europium-labeled zearalenone monoclonal antibody and the europium-labeled sterigmatocystin monoclonal antibody into a 0.01 mol/L phosphoric acid buffer solution containing 1.5% (m/v) of trehalose and 2% (m/v) of bovine serum albumin, of which the pH is 8.2, placing a certain volume of each of the prepared solutions in the sample reaction bulb, and performing freeze-drying in a freeze dryer, thereby obtaining the sample reaction bulb for later use. The content of an europium-labeled aflatoxin B1 monoclonal antibody freeze-dried product in the sample reaction bulb is 0.2 μg the content of an europium-labeled fumonisin B1 monoclonal antibody freeze-dried product in the sample reaction bulb is 0.3 μg, the content of an europium-labeled ochratoxin A monoclonal antibody freeze-dried product in the sample reaction bulb is 0.25 μg, the content of an europium-labeled zearalenone monoclonal antibody freeze-dried product in the sample reaction bulb is 0.2 μg, and the content of an europium-labeled sterigmatocystin monoclonal antibody freeze-dried product in the sample reaction bulb is 0.3 μg;

Application of an immunochromatographic time-resolved fluorescence detecting kit for simultaneously detecting mixed pollution of aflatoxin B1, fumonisin B1, ochratoxin A, zearalenone and sterigmatocystin in detection on the aflatoxin B1, the fumonisin B1, the ochratoxin A, the zearalenone and the sterigmatocystin in a feedstuff sample:

Taking and adding 20 g of confirmed negative feedstuff sample into 100 mL of 70% (volume percent) methanol solution, performing homogenization for 2 min, performing standing, performing filtering with double-layer filter paper, collecting 1 mL of filter liquor, adding 5 mL of sample diluent to dilute the filter liquor, and performing uniform mixing, thereby obtaining a blank matrix solution;

Preparing 6 mixed standard solutions of aflatoxin B1, ochratoxin A, zearalenone and fumonisin B1, of which concentration gradients are separately corresponding to those as follows: aflatoxin B1 (0 ng/mL, 0.05 ng/mL, 0.1 ng/mL, 0.25 ng/mL, 0.5 ng/mL and 1.0 ng/mL), fumonisin B1 (0 ng/mL, 0.05 ng/mL, 0.1 ng/mL, 0.25 ng/mL, 0.5 ng/mL and 1.0 ng/mL), ochratoxin A (0 ng/mL, 0.25 ng/mL, 0.5 ng/mL, 1.0 ng/mL, 2 ng/mL and 4 ng/mL), zearalenone (0 ng/mL, 0.5 ng/mL, 1.0 ng/mL, 2.5 ng/mL, 5.0 ng/mL and 10 ng/mL) and sterigmatocystin (0 ng/mL, 0.05 ng/mL, 0.1 ng/mL, 0.25 ng/mL, 0.5 ng/mL and 1.0 ng/mL), to prepare gradient mixed standard solutions. Repeating 5 times at each concentration point of each standard solution, performing detecting with a poly-toxin detecting test strip, and performing detecting with a time-resolved fluorescence detector: adding 150 μL of each of the standard solutions into a sample reaction bulb, performing uniform mixing, inserting an immunochromatographic time-resolved fluorescence test strip, performing a reaction for 6 min at a temperature of 37° C., sucking off residual liquid from a sample pad with absorbent paper, performing detecting with a time-resolved fluoroimmunoassay analyzer immediately (excitation wavelength: 365 nm, and assay wavelength: 615 nm), reading a fluorescence signal intensity value of a detected region, and calculating an average value of repeating of 5 times. A standard curve is drawn according to napierian logarithms (Lnc) of standard-series concentration values and (T/C) of fluorescence signal intensity value of each T line/fluorescence signal intensity value of a C line, an equation of the standard curve is represented by Y=a*lnc+b, and standard curve parameters of 5 kinds of detected objects are shown in a table as follows:

|  | a | b | $R^2$ | Detection limit/ng/mL |
|---|---|---|---|---|
| aflatoxin B1 | −1.425 | 3.524 | 0.991 | 0.06 |
| fumonisin B1 | −1.750 | 3.448 | 0.989 | 0.2 |
| ochratoxin A | −1.594 | 4.788 | 0.989 | 0.5 |
| zearalenone | −1.750 | 5.751 | 0.979 | 1.0 |
| sterigmatocystin | −1.643 | 3.364 | 0.976 | 0.3 |

Taking and adding 20 g of a feedstuff sample to be detected into 100 mL of 70% (volume percent) methanol solution, performing homogenization for 2 min, performing standing, performing filtering with double-layer filter paper, collecting 1 mL of filter liquor, adding 5 mL of sample diluent to dilute the filter liquor, and performing uniform mixing; taking and adding 150 μL of a detecting solution of the feedstuff sample to be detected into a sample reaction bulb, performing uniform mixing, inserting an immunochromatographic time-resolved fluorescence test strip, performing a reaction for 6 min at a temperature of 37° C., sucking off residual liquid from a sample pad with absorbent paper, performing detecting with a time-resolved fluoroimmunoassay analyzer immediately (excitation wavelength: 365 nm, and assay wavelength: 615 nm) to obtain ratios (T/C) of time-resolved fluorescence intensity of each of the 5 test lines of the immunochromatographic time-resolved fluorescence test strip to time-resolved fluorescence intensity of the quality control line, then, separately substituting the ratios (T/C) into relationship curves between the ratios (T/C) of the fluorescence intensity of the test lines of the immunochromatographic time-resolved fluorescence test strip to the fluorescence intensity of the quality control line and concentrations of the aflatoxin B1, the fumonisin B1, the ochratoxin A, the zearalenone and the sterigmatocystin, thereby obtaining that the content of the aflatoxin B1 in the feedstuff sample is 6.4 μg/kg, the content of the fumonisin B1 in the feedstuff sample is 4.1 μg/kg, the content of the ochratoxin in the feedstuff sample is 0 μg/kg, the content of the zearalenone in the feedstuff sample is 0 μg/kg, and the content of the sterigmatocystin in the feedstuff sample is 3.3 μg/kg.

Embodiment 7

The difference from the embodiment 6 is as follows: in the immunochromatographic time-resolved fluorescence test strip, the absorbent pad has a length of 14 mm and a width of 3 mm; the test pad has a length of 30 mm and a width of 3 mm; the sample pad has a length of 16 mm and a width of 3 mm, and an overlapped length among all the adjacent pads is 2 mm; and a spacing between the test line, close to the quality control line, on the test pad of the fluorescence test strip and the upper edge of the cellulose nitrate film is 8 mm, a spacing between every two adjacent test lines is 4 mm. A test line per centimeter on the test pad of the immunochromatographic time-resolved fluorescence test strip is coated with 200 ng of the aflatoxin B1-bovine serum albumin conjugate, a test line per centimeter is coated with 250 ng of the fumonisin B1-bovine serum albumin conjugate, a test line per centimeter is coated with 200 ng of the ochratoxin A-bovine serum albumin conjugate, a test line per centimeter is coated with 250 ng of the zearalenone-bovine serum albumin conjugate, and a test line per centimeter is coated with 300 ng of the sterigmatocystin-bovine serum albumin conjugate; and the quality control line per centimeter is coated with 150 ng of the rabbit antimouse polyclonal antibody; the content of the europium-labeled aflatoxin B1 monoclonal antibody freeze-dried product in the sample reaction bulb is 0.2 μg the content of the europium-labeled fumonisin B1 monoclonal antibody freeze-dried product in the sample reaction bulb is 0.3 μg the content of the europium-labeled ochratoxin A monoclonal antibody freeze-dried product in the sample reaction bulb is 0.3 μg the content of the europium-labeled zearalenone monoclonal antibody freeze-dried product in the sample reaction bulb is 0.2 μg and the content of the europium-labeled sterigmatocystin monoclonal antibody freeze-dried product in the sample reaction bulb is 0.3 μg.

Taking a feedstuff sample containing a variety of toxins, which is confirmed through high-performance liquid chromatography (the content of Aflatoxin B1 is 5.1 μg/kg, the content of Fumonisin B1 is 3.9 μg/kg, the content of Ochratoxin is 1.5 μg/kg, the content of Zearalenone is 41.2 μg/kg, and the content of Sterigmatocystin is 5.3 μg/kg).

Taking and adding 10 g of a feedstuff sample to be detected into 30 mL of 70% (volume percent) methanol solution, performing homogenization for 2 min, performing standing, performing filtering with double-layer filter paper, collecting 1 mL of filter liquor, adding 9 mL of sample diluent to dilute the filter liquor, and performing uniform mixing; taking and adding 150 μL of a detecting solution of the feedstuff sample to be detected into a sample reaction bulb, performing uniform mixing, inserting an immunochromatographic time-resolved fluorescence test strip, performing a reaction for 6 min at a temperature of 37° C., sucking off residual liquid from a sample pad with absorbent paper, performing detecting with a time-resolved fluoroimmunoassay analyzer immediately (excitation wavelength: 365 nm, and assay wavelength: 615 nm) to obtain ratios (T/C) of time-resolved fluorescence intensity of each of the 5 test lines of the immunochromatographic time-resolved fluorescence test strip to time-resolved fluorescence intensity of the quality control line, then, separately substituting the ratios (T/C) into relationship curves between the ratios (T/C) of the fluorescence intensity of the test lines of the immunochromatographic time-resolved fluorescence test strip to fluorescence intensity of the quality control line and concentrations of the aflatoxin B1, the fumonisin B1, the ochratoxin A, the zearalenone and the sterigmatocystin, thereby obtaining that the content of the aflatoxin B1 in the feedstuff sample is 5.3 μg/kg, the content of the Fumonisin B1 in the feedstuff sample is 3.7 μg/kg, the content of the ochratoxin in the feedstuff sample is 1.8 μg/kg, the content of the zearalenone in the feedstuff sample is 41.8 μg/kg, and the content of the sterigmatocystin in the feedstuff sample is 5.7 μg/kg.

What is claimed is:

1. An immunochromatographic time-resolved fluorescence kit for simultaneously detecting mixed pollution of aflatoxin B1, fumonisin B1, ochratoxin A, zearalenone and sterigmatocystin, comprising:

an immunochromatographic time-resolved fluorescence test strip and a sample reaction bulb containing an europium-labeled aflatoxin B1 monoclonal antibody freeze-dried product, an europium-labeled fumonisin B1 monoclonal antibody freeze-dried product, an europium-labeled ochratoxin A monoclonal antibody freeze-dried product, an europium-labeled zearalenone monoclonal antibody freeze-dried product and an europium-labeled sterigmatocystin monoclonal antibody freeze-dried product, wherein the immunochromatographic time-resolved fluorescence test strip comprises a PVC substrate, an absorbent pad, a test pad and a sample pad sequentially stuck to one face of the substrate from top to bottom, all the adjacent pads are in overlapped connection at joints, the test pad employs a cellulose nitrate film as a base pad, a transverse quality control line and 5 test lines are arranged on the cellulose nitrate film from top to bottom, the quality control line is coated with a rabbit antimouse polyclonal antibody, the 5 test lines are separately coated with an aflatoxin B1-bovine serum albumin conjugate, a fumonisin B1-bovine serum albumin conjugate, an ochratoxin A-bovine serum albumin conjugate, a zearalenone-bovine serum albumin conjugate and a sterigmatocystin-bovine serum albumin conjugate, and wherein said aflatoxin B1 monoclonal antibody is secreted from hybridoma cell line 3G1 that is deposited with an accession number of CCTCC NO. C201014;

said fumonisin B1 monoclonal antibody is secreted from a hybridoma cell line Fm7A11that is deposited with an accession number of CCTCC NO. C201636;

said ochratoxin A monoclonal antibody is secreted from hybridoma cell line 1H2 that is deposited with an accession number of CCTCC NO. C201329;

said zearalenone monoclonal antibody is secreted from hybridoma cell line 2D3 that is deposited with accession number of CCTCC NO. C201328; and said sterigmatocystin monoclonal antibody is secreted from hybridoma cell line ST03that is deposited with an accession number of CCTCC NO. C2013187.

2. The immunochromatographic time-resolved fluorescence kit according to claim 1, wherein in the immunochromatographic time-resolved fluorescence test strip, the absorbent pad has a length of 10-16 mm and a width of 3-5 mm; the test pad has a length of 25-33 mm and a width of 3-5 mm; the sample pad has a length of 12-18 mm and a width of 3-5 mm, and an overlapped length among all the adjacent pads is 1-2 mm; a spacing between the test line, close to the quality control line, on the test pad of the immunochromatographic time-resolved fluorescence test strip and the upper edge of the cellulose nitrate film is 5-10 mm, a spacing between every two adjacent test lines is 1.5-4.5 mm, and a spacing between the test line close to the quality control line and the quality control line is 3-6 mm; and the sample reaction bulb is a 1-5 mL bayonet bottle.

3. The immunochromatographic time-resolved fluorescence kit according to claim 1, wherein a test line per centimeter on the test pad of the immunochromatographic time-resolved fluorescence test strip is coated with 100-400 ng of the aflatoxin B1-bovine serum albumin conjugate, a test line per centimeter is coated with 100-400 ng of the fumonisin B1-bovine serum albumin conjugate, a test line per centimeter is coated with 100-400 ng of the ochratoxin A-bovine serum albumin conjugate, a test line per centimeter is coated with 100-400 ng of the zearalenone-bovine serum albumin conjugate, and a test line per centimeter is coated with 100-400 ng of the sterigmatocystin-bovine serum albumin conjugate; and the quality control line per centimeter is coated with 80-200 ng of the rabbit antimouse polyclonal antibody.

4. The immunochromatographic time-resolved fluorescence kit according to claim 1, wherein a content of the europium-labeled aflatoxin B1 monoclonal antibody freeze-dried product in the sample reaction bulb is 0.1-0.3 μg, the content of the europium-labeled fumonisin B1 monoclonal antibody freeze-dried product in the sample reaction bulb is 0.1-0.3 μg, the content of the europium-labeled ochratoxin A monoclonal antibody freeze-dried product in the sample reaction bulb is 0.1-0.3 μg, the content of the europium-labeled zearalenone monoclonal antibody freeze-dried product in the sample reaction bulb is 0.1-0.3 μg, and the content of the europium-labeled sterigmatocystin monoclonal antibody freeze-dried product in the sample reaction bulb is 0.1-0.3 μg.

* * * * *

SEQUENCE LISTING

```
<160> NUMBER OF SEQ ID NOS: 4

<210> SEQ ID NO 1
<211> LENGTH: 379
<212> TYPE: DNA
<213> ORGANISM: mouse

<400> SEQUENCE: 1
caggtgcagc    tgaaggagtc    aggacctggc    ctggtggcgc    cctcacagag         50
cctgtccatc    acttgcactg    tctctgggct    ttcattaacc    agctatggtg        100
tacactgggt    tcgtcaggcc    ccaggaaagg    gtctggagtg    gctgggagta        150
atttggggtg    gtggaaacac    aaattataat    tcggctctca    tgtccagact        200
gagcatcagc    aaagacaact    ccaggagcca    agttttctta    agaatgaaca        250
gtctgcaaat    tgatgacaca    gccatgtact    attgtgccag    aggcaggatg        300
gactactggg    gtcaaggaac    ctcagtcacc    gtctcgtcag    ccaaaacgac        350 accccatct     gtctatccac    tggcccctg                                    379
```

<210> SEQ ID NO 2
<211> LENGTH: 348
<212> TYPE: DNA
<213> ORGANISM: mouse

<400> SEQUENCE: 2

```
gacatcaaga   tgacccagtc   tccatcttcc   atgtatgcat   ctctaggaga      50
aagagtcact   atcacttgca   aggcgagtca   ggacattagt   agctatttag     100
gctggttaca   gcagaaacca   gggaaatctc   ctaagaccct   gatctatcgt     150
gcaaacacat   tggtagaagg   ggtcccatcc   agattcagtg   gcagtggatc     200
tggggaagat   tattctctca   ccatcagcag   cctggagtat   gaagatatgg     250
gaatttatta   ttgtctacag   tatgatgagt   ttccgtacac   gttcggaggg     300
gggaccaagc   tggaaataaa   acgggctgat   gctgcaccaa   ctgtatcc       348
```

<210> SEQ ID NO 3
<211> LENGTH: 126
<212> TYPE: PRT
<213> ORGANISM: mouse

<400> SEQUENCE: 3

Gln Val Gln Leu Lys Glu Ser Gly Pro Gly Leu Val Ala Pro Ser
1               5                  10                  15

Gln Ser Leu Ser Ile Thr Cys Thr Val Ser Gly Leu Ser Leu Thr
                20                  25                  30

Ser Tyr Gly Val His Trp Val Arg Gln Ala Pro Gly Lys Gly Leu
                35                  40                  45

Glu Trp Leu Gly Val Ile Trp Gly Gly Gly Asn Thr Asn Tyr Asn
                50                  55                  60

Ser Ala Leu Met Ser Arg Leu Ser Ile Ser Lys Asp Asn Ser Arg
                65                  70                  75

Ser Gln Val Phe Leu Arg Met Asn Ser Leu Gln Ile Asp Asp Thr
                80                  85                  90

Ala Met Tyr Tyr Cys Ala Arg Gly Arg Met Asp Tyr Trp Gly Gln
                95                 100                 105

Gly Thr Ser Val Thr Val Ser Ser Ala Lys Thr Thr Pro Pro Ser
                110                115                 120

Val Tyr Pro Leu Ala Pro
                125

<210> SEQ ID NO 4
<211> LENGTH: 116
<212> TYPE: PRT
<213> ORGANISM: mouse

<400> SEQUENCE: 4

Asp Ile Lys Met Thr Gln Ser Pro Ser Ser Met Tyr Ala Ser Leu
1               5                  10                  15

Gly Glu Arg Val Thr Ile Thr Cys Lys Ala Ser Gln Asp Ile Ser
                20                  25                  30

Ser Tyr Leu Gly Trp Leu Gln Gln Lys Pro Gly Lys Ser Pro Lys
                35                  40                  45

Thr Leu Ile Tyr Arg Ala Asn Thr Leu Val Glu Gly Val Pro Ser
                50                  55                  60

Arg Phe Ser Gly Ser Gly Ser Gly Glu Asp Tyr Ser Leu Thr Ile
                65                  70                  75

-continued

```
Ser Ser Leu Glu Tyr Glu Asp Met Gly Ile Tyr Tyr Cys Leu Gln
                80              85                  90

Tyr Asp Glu Phe Pro Tyr Thr Phe Gly Gly Gly Thr Lys Leu Glu
                95              100                 105

Ile Lys Arg Ala Asp Ala Ala Pro Thr Val Ser
                110             115
```